United States Patent [19]

Baxter et al.

[11] 4,338,121
[45] Jul. 6, 1982

[54] LOOSENING AGENTS FOR FRUIT OF PLANTS

[75] Inventors: Robert Baxter, Sittingbourne, England; Ronald W. A. Leach, Kingwood, Tex.

[73] Assignee: Shell Oil Company, Houston, Tex.

[21] Appl. No.: 182,184

[22] Filed: Aug. 28, 1980
(Under 37 CFR 1.47)

[30] Foreign Application Priority Data

Aug. 28, 1979 [GB] United Kingdom ............... 7929767

[51] Int. Cl.³ .............................................. A01N 37/18

[52] U.S. Cl. ............................................. 71/118; 71/70
[58] Field of Search ..................................... 71/118, 70

[56] References Cited

U.S. PATENT DOCUMENTS 3,634,509 1/1972 Yates et al. ........................... 71/118
4,218,239 8/1980 Entwistle ............................. 71/118

Primary Examiner—Catherine L. Mills

[57] ABSTRACT

Certain propionamides are used for loosening fruit of plants.

3 Claims, No Drawings

LOOSENING AGENTS FOR FRUIT OF PLANTS

The present invention relates to a method of loosening fruit on plants.

BACKGROUND OF THE INVENTION

A very high proportion of the cost of fruit results from the cost of harvesting. Hand-picking of fruit is extremely expensive, with the result that mechanical devices for picking have been developed. Such devices generally work by shaking the tree to cause the fruit to fall. If the fruit is tighly bound to the tree, this operation is inefficient and may cause severe damage to the tree, often reducing the yield the following year.

There is thus a need for the use of chemical fruit loosening, or abscission, agents. Such agents are plant growth regulants which reduce the strength of attachment of the fruit to the tree, and thus aid mechanical harvesting.

DESCRIPTION OF THE INVENTION it has now been found that certain aniline derivatives effect the loosening of fruit on plants, the invention therefore providing a method of loosening fruit on a plant, which comprises treating the plant or part thereof with an amount effective for that purpose of a compound of the formula

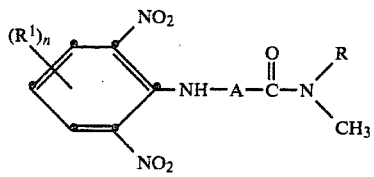

wherein A is —CH$_2$—CH$_2$— or —CH(CH$_3$)—, R is hydrogen or hydroxyl and n is zero or one, with the proviso that when A is —CH$_2$—CH$_2$—, n is zero, and when A is —CH(CH$_3$)—

(a) R is hydrogen or hydroxyl and (R$^1$)n is 4-methyl, or (b) R is hydrogen, and (R$^1$)n is 3-acetylamino, or is 4-fluoro.

Because of their effectiveness as loosening agents, preferred compounds of Formula I are those which A is —CH(CH$_3$)—, R is hydrogen or hydroxyl, n is 1 and R$^1$ is 4-methyl.

The compounds of Formula I in which A is —CH(CH$_3$)— exist in optical isomeric form. The method of the present invention may be carried out using either the D or the L isomer or a mixture thereof. In general, the D isomer or mixtures containing the D isomer are preferred.

The compounds of Formula I can be prepared by reacting a compound of the formula

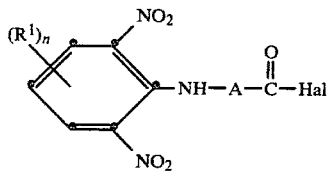

in which Hal is halogen, preferably chlorine, with a compound of the formula

N(H)(R)(CH$_3$)    (III)

If the reaction is carried out using a single optical isomer, preferably the D-isomer, of a compound of Formula II in which A is —CH(CH$_3$)—, the corresponding single optical isomer of the compound of Formula I is obtained.

The compound of Formula II may be obtained by reaction of the corresponding free carboxylic acid with a halogenating agent, for example thionyl chloride.

The free carboxylic acid may be obtained be reacting a compound of the general formula

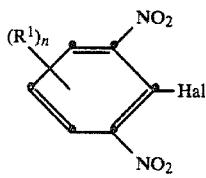

with a compound of the formula

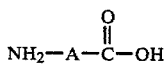

This reaction is suitably carried out in the presence of an acid binding agent, for example an alkali metal carbonate, bicarbonate or hydroxide, or an amine, preferably a tertiary amine, for example pyridine. If a single optical isomer (preferably the L-isomer) of a compound of formula V is used, the reaction proceeds with inversion of configuration to produce the opposite isomer (preferably the D-isomer), of the resulting acid.

Compounds of the class described in Formula I, and methods for their preparation, are described in U.S. Pat. No. 3,634,509.

Preparation of compounds of Formula I in particular instances is described in the following examples. In such case, the identity of the product was confined by appropriate chemical and spectral analyses.

EXAMPLE 1

N-methyl-2-(4-methyl-2,6-dinitroanilino)propionamide (1) and its D-isomer (2)

A mixture of 810 g of 4-chloro-3,5-dinitrotoluene, 384 g of dl-alpha-alanine, and 840 g of sodium bicarbonate was stirred and refluxed in 8 l of 95% ethanol for 18 hours. The mixture was diluted with water, filtered, and the ethanol was distilled off under reduced pressure. 1 l of water was added during the distillation in order to maintain the solids in solution. The aqueous solution was cooled by the addition of 2 kg of ice and acidified with concentrated hydrochloric acid (Congo Red) whilst stirring. The initially formed sticky precipitate crystallized on continued stirring to a dark-yellow solid which was filtered off, washed with water, and air-dried to give 2-(4-methyl-2,6-dinitroanilino)propionic acid (1 A), m.p.: 158°-161° C.

A solution 490 g of 1 A in 2.5 l of benzene was stirred and 570 g of thionyl chloride was added at a rate such that a smooth evolution of gases occurred. When the addition was complete stirring was continued, and the mixture was refluxed for 12 hours. The reaction mixture was then filtered, and the benzene and excess thionyl chloride were distilled off under reduced pressure. The acid chloride remained as a dark red oil.

This oil was dissolved in 2.5 l of methylene chloride and the solution cooled to 0° C. 160 g of methylamine was dissolved in 1 l of methylene chloride and the solution was added to the solution of the acid chloride with stirring at 0°–5° C. The precipitate was filtered off, and washed with methylene chloride. The filtrate was evaporated to dryness, and the residue was stirred with 1 l of industrial methylated spirit. The product was filtered off, washed with industrial methylated spirit and air-dried, to give 1, as a yellow powder, m.p.: 149°–151° C.

The D-isomer of this compound, (2, m.p.: 135°–136° C.) was produced by a method analogous to that used for the preparation of the dl-racemic mixture, except that l-alpha-alanine was used as starting material.

EXAMPLE 2

N-methyl-2-(4-methyl-2,6-dinitroanilino)propionohydroxamic acid (3) and its D-isomer (4)

A solution of 2.0 g of 2-(4-methyl-2,6-dinitroanilino)-propionyl chloride, prepared as in Example 1, in 50 ml of methylene chloride was added dropwise to a stirred solution of 2.0 g of N-methylhydroxylamine hydrochloride and 6.0 g of sodium acetate in 50 ml of water at 0°–5° C. The mixture was stirred for 2 hours, after which the organic layer was speareated, dried and evaporated to dryness. The yellow residue was recrystallised from benzene to give 3, m.p.: 171°–172° C.

The D-isomer of 3 (4, m.p.: 125°–126° C.) was prepared by a method analogous to that used for the preparation of the dl racemic mixture, except that l-alpha-alanine was used as starting material.

In a similar manner there were prepared the following Compounds wherein, referring to Formula 1, the respective moieties were:

| Compound | Moiety A | n | (R)$_n$ | R |
|---|---|---|---|---|
| 5 | —CH$_2$—CH$_2$— | 0 | — | H |
| 6 | —CH(CH$_3$)— | 1 | 3-acetylamino | H |
| 7 | —CH(CH$_3$)— | 1 | 4-fluoro | H |

The method of the invention may, for example, be used for loosening the fruit in crops of citrus fruits, apples, olives, grapes, nuts and coffee. It is especially useful for the treatment of oranges and olives. Suitable the active compound is applied to the plant during the period of time of 3 days to 3 weeks before harvest of the fruit is desired. Depending on the dosage applied, the crop treated, and the period of time before harvesting, varying proportions of fruit may actually fall spontaneously from the plant. In some crops it may be desirable to reduce the strength of attachment of the fruit to the plant without actually causing fruit drop. In other crops, notably olives, it may be desirable to cause the fruit to fall from the plant spontaneously under its own weight, for ease of harvesting.

The degree of loosening obtained will depend on various factors, including the dosage of active compound applied.

The optimum dosage of the compound of Formula I applied to the plant will depend on such factors as the time of year, the temperature and the humidity, and, of course, the particular plant being treated. Generally, however, the compound of the general Formula I is most suitably applied in the form of a solution containing from 5 to 2000 ppm, preferably 50 to 500 ppm, of the compound.

The volume of solution applied will depend very much on the lay-out of the area being treated, but will generally be selected such that each plant is treated with from 5 milligrams to 40 grams of the compound of Formula I. For fruit loosening, for example in orchards or vineyards, each plant is preferably treated with from 5 milligrams to 20 grams of the compound.

The dosage applied should not, of course, be so large that the plant is significantly damaged by the possible herbicidal effect of the compound of Formula I.

The compounds of Formula I may, if desired, be applied to the plant with other loosening agents.

Suitably, the compound of Formula I is formulated as a composition which, in addition to the compound of Formula I and optionally other active ingredients, contains a carrier or a surface-active agent or both a carrier and a surface-active agent. Suitable formulations are described for example in British Patent Specification No. 1,164,160.

The following Examples illustrate performance of the invention in particular instances.

EXAMPLE 3

Field Tests for Abscission Activity

Tests were carried out to determine the activity of compounds of the invention as fruit abscission agents. Each compound was formulated as a solution in acetone-water (1:1 v:v) with 0.05% of Nonidet P40 (Trade Mark) added as wetting agent.

Branches of trees carrying a convenient number of ripe fruits were sprayed with 500 milliliters of solutions containing various concentrations of the test compounds. For each type of fruit, a commercial compound known as an abscission agent for that fruit also was tested. Control branches were sprayed with 500 milliliters of a blank solution (i.e., acetone, water and wetting agent only). At the end of the test period, the average force required to pull a fruit from the branch was measured.

Tests were carried out on oranges (variety "Valencia Late") with a test period of 5 days, olives (variety "Martena") with a test period of 11 days, and almonds, with a test period of 7 days. The compounds tested were as follows, and the tests results are given in Table 1.

TABLE 1

| | | Test Results | | | | | | | |
|---|---|---|---|---|---|---|---|---|---|
| | | Mean force required to remove fruit (% of control) | | | | | | | |
| Compound | (ppm) | Oranges | | | Olives | | Apples | | Almonds | |
| No. | → | 50 | 250 | 1000 | 250 | 750 | 250 | 1000 | 250 | 1000 |
| 1 | | 52.6 | 3.5 | 5.0 | 31.3 | 30.1 | 22.7 | 23.9 | 72.9 | 39.0 |
| 2 | | 6.8 | 5.0 | 0.6 | 31.3 | 37.7 | 35.5 | 18.4 | 37.6 | 66.1 |
| 3 | | 59.3 | 36.7 | 20.9 | 28.0 | 36.0 | 73.1 | 44.0 | 85.4 | 88.1 |
| 4 | | 21.5 | 18.4 | — | 41.3 | 32.9 | 36.8 | 25.9 | 45.8 | 55.6 |

TABLE 1-continued

| Compound No. | (ppm) → | Test Results Mean force required to remove fruit (% of control) | | | | | | | |
|---|---|---|---|---|---|---|---|---|---|
| | | Oranges | | | Olives | | Apples | | Almonds | |
| | | 50 | 250 | 1000 | 250 | 750 | 250 | 1000 | 250 | 1000 |
| "RELEASE" | | 88.6 | 99.9 | 73.0 | | | | | 84.7 | |
| "ALSOL-200" | | | | | 86.6 | 47.0 | | | | |
| "ETHREL" | | | | | | | 101.7 | 76.7 | | |

"RELEASE" - Trade Mark - (Abott) 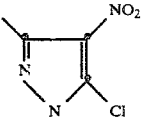

"ALSOL-200" - Trade Mark - Cl—CH$_2$—CH$_2$—Si(—O—CH$_2$—CH$_2$—O—CH$_3$)$_3$ (Ciba-Geigy)
"ETHREL" - Trade Mark - Cl—CH$_2$—CH$_2$—PO$_3$H$_2$ (Amchem)

It can be seen from Table 1 that, for olives, oranges, apples and almonds, application of a compound of Formula 1 resulted in a considerable reduction of the force required to remove the fruit from the tree. Furthermore, in every test except for a single test on almonds, the compound of Formula 1 gave a greater reduction in the force required to remove the fruit, than a commercially available fruit abscission agent.

Similar tests were performed on the abscission of coffee beans, with similar results.

EXAMPLE 4

In a laboratory test carried out to investigate the abscission activity of various compounds, the following procedure was used.

French bean (cv. Canadian Wonder) were used as the indicator species for abscission activity. French bean seeds were sown at the rate of 2 per 8 centimeter pot in sterilized loam. Plants were maintained at 20° C. under 14 hour daylength and watered by subirrigation. At the first trifoliate leaf stage of development, the laminae of the primary leaves were removed. 48 hours after removal of the laminae, liquid formulations of the test compounds were applied. The formulation used, consisted of 90% water and 10% acetone which contained 0.4% TRITON X155 and amounts of the test compound to give spray application at various dosages up to 2000 ppm.

Treatments were as foliar applications to "run off" using a fixed nozzle. After treatment the plants were set out in randomised block design.

All of compounds 1 through 7 gave greater than 75% activity, compared with untreated controls.

I claim as my invention:

1. A method of loosening fruit on a plant, which comprises treating the fruit-bearing plant or part thereof with an amount effective for the purpose of a compound of the formula

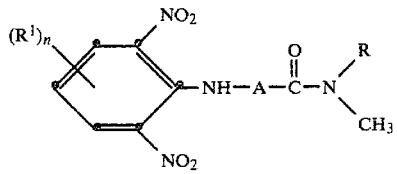

wherein A is —CH$_2$—CH$_2$— or —CH(CH$_3$)—, R is hydrogen or hydroxyl and n is zero or one, with the proviso that when A is —CH$_2$—CH$_2$—, n is zero, and when A is —CH(CH$_3$)—

(a) R is hydrogen or hydroxyl and (R$^1$)n is 4-methyl, or
(b) R is hydrogen, and (R$^1$)n is 3-acetylamino, or is 4-fluoro.

2. A method as defined in claim 1 in which A is —CH(CH$_3$)—, R is hydrogen or hydroxyl, n is 1 and R$^1$ is 4-methyl.

3. A method as defined in claim 2, in which the plant is one of citrus, apple, olive, grapes, nuts and coffee.

* * * * *